United States Patent [19]

Cheung et al.

[11] Patent Number: 5,259,381

[45] Date of Patent: * Nov. 9, 1993

[54] APPARATUS FOR THE AUTOMATIC CALIBRATION OF SIGNALS EMPLOYED IN OXIMETRY

[75] Inventors: Peter W. Cheung, Mercer Island; Karl F. Gauglitz, Kirkland; Scott W. Hunsaker, Seattle; Stephen J. Prosser, Lynnwood; Darrell O. Wagner, Monroe; Robert E. Smith, Edmonds, all of Wash.

[73] Assignee: Physio-Control Corporation, Redmond, Wash.

[*] Notice: The portion of the term of this patent subsequent to Apr. 3, 2007 has been disclaimed.

[21] Appl. No.: 377,722

[22] Filed: Jul. 10, 1989

Related U.S. Application Data

[63] Continuation of Ser. No. 897,663, Aug. 18, 1986, Pat. No. 4,913,150.

[51] Int. Cl.⁵ .............................................. A61B 5/00
[52] U.S. Cl. .................................... 128/633; 128/666; 356/41
[58] Field of Search ................ 128/633, 634, 664–667; 330/59, 308; 250/214 A

[56] References Cited

U.S. PATENT DOCUMENTS

| | | | |
|---|---|---|---|
| 3,709,612 | 1/1973 | Clemens | 128/633 |
| 4,586,513 | 5/1986 | Hamaguri | 128/633 |
| 4,685,464 | 8/1987 | Goldberger et al. | 128/633 |
| 4,710,631 | 12/1987 | Aotsuka et al. | 250/354.1 |
| 4,723,554 | 2/1988 | Oman et al. | 128/664 |

FOREIGN PATENT DOCUMENTS 0104772 4/1984 European Pat. Off. ............ 128/633

*Primary Examiner*—Lee S. Cohen
*Assistant Examiner*—Robert L. Nasser, Jr.
*Attorney, Agent, or Firm*—Christensen, O'Connor, Johnson & Kindness

[57] ABSTRACT

Under the present invention, a method and apparatus are provided for compensating for the effect temperature variations have on the wavelength of light emitted by the oximeter sensor light source (40, 42). In pulse oximetry, LEDs (40, 42) are typically employed to expose tissue to light at two different wavelengths. The light illuminating the tissue is received by a detector (38) where signals proportional to the intensity of light are produced. These signals are then processed by the oximeter circuitry to produce an indication of oxygen saturation. Because current oximetry techniques are dependent upon the wavelengths of light emitted by the LEDs (40, 42), the wavelengths must be known. Even when predetermined combinations of LEDs (40, 42) having relatively precise wavelengths are employed, variations in the wavelength of light emitted may result. Because the sensor (12) may be exposed to a significant range of temperatures while in use, the effect of temperature on the wavelengths may be significant. To compensate for this effect, a temperature sensor (50) is included in the sensor (12) to produce a signal indicative of sensor temperature. This signal is interpreted by the oximeter circuitry including, for example, a microcomputer (16), where the effect of temperature on wavelength is compensated for. In a preferred arrangement, this compensation takes the form of a computation of an alternative calibration curve from which the oxygen saturation is indicated, given a particular processing of signals from the detector (38).

3 Claims, 9 Drawing Sheets

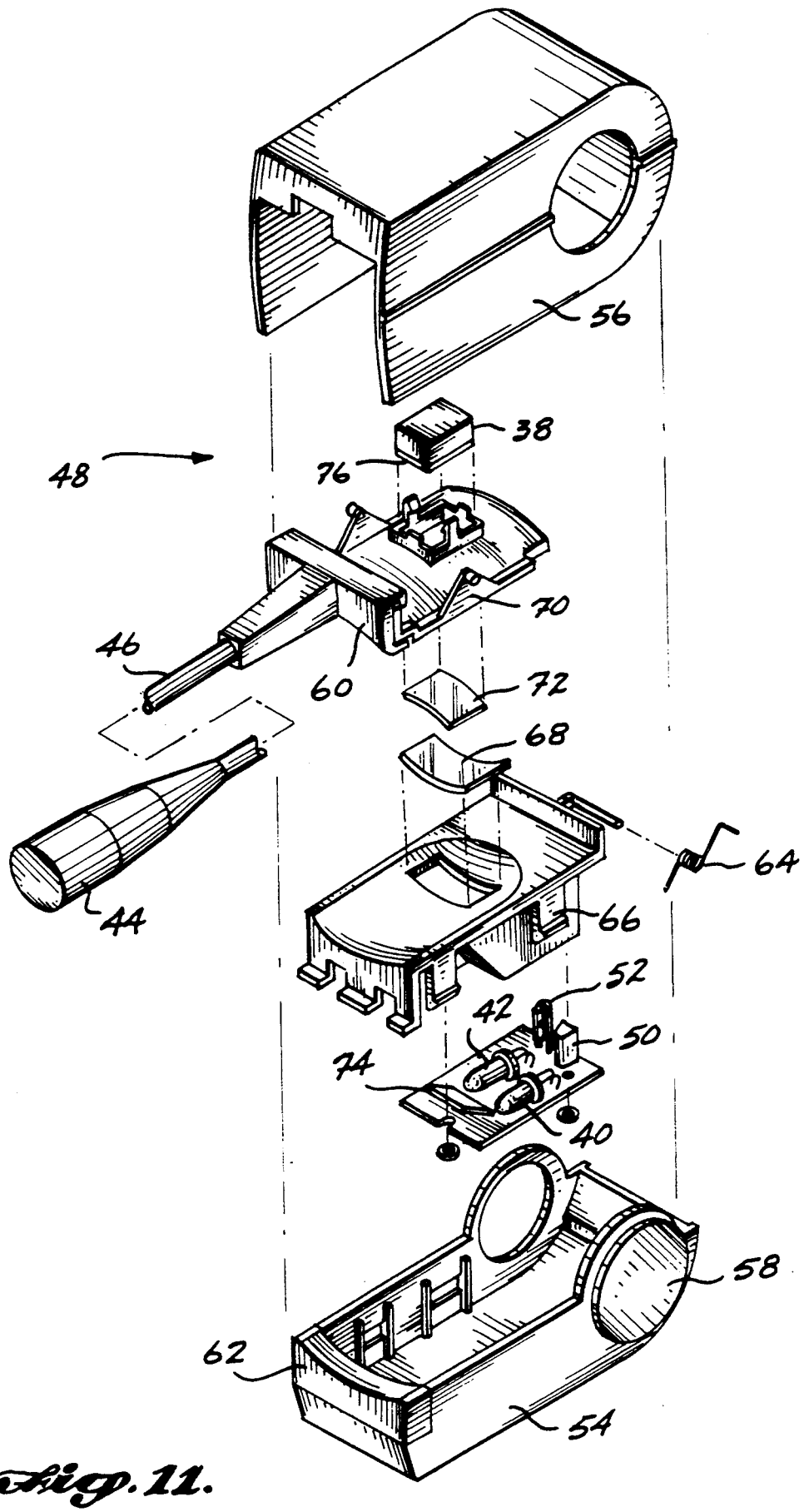

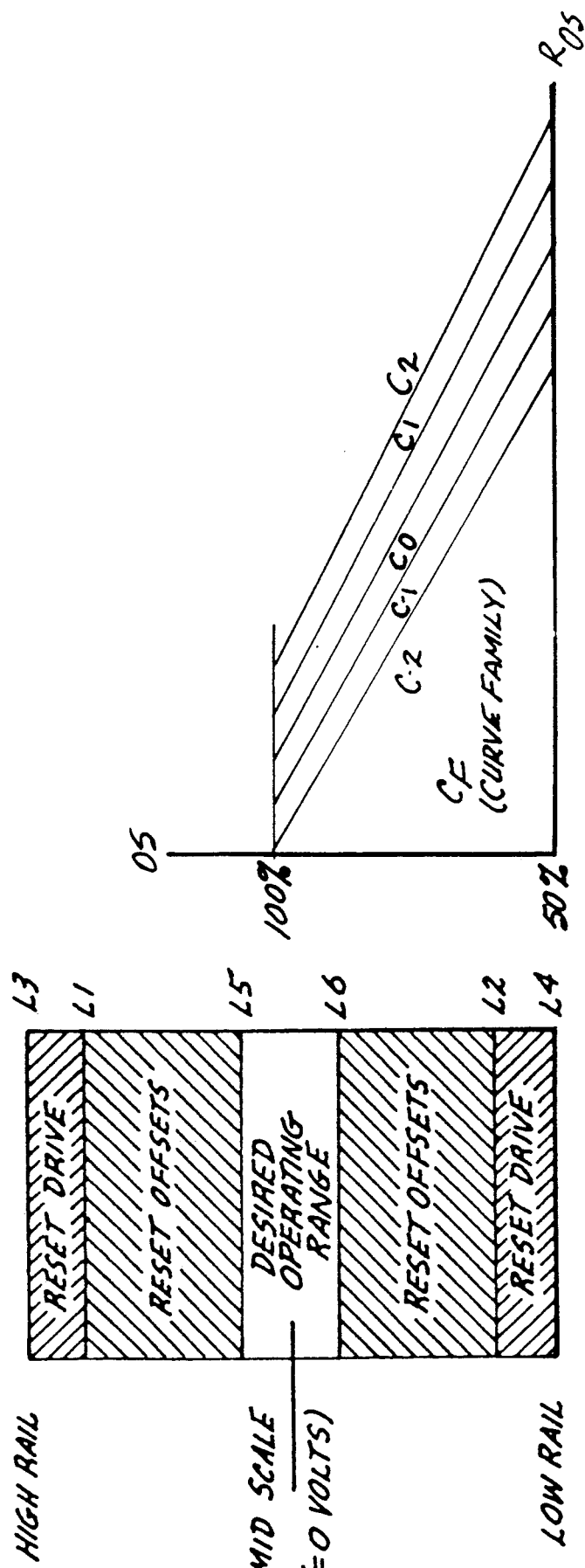

APPARATUS FOR THE AUTOMATIC CALIBRATION OF SIGNALS EMPLOYED IN OXIMETRY

This is a continuation of the prior application Ser. No. 897,663, filed Aug. 18, 1986, the benefit of the filing date of which is hereby claimed under 35 USC 120, now U.S. Pat. No. 4,913,150.

BACKGROUND OF THE INVENTION

This invention relates to oximetry and, more particularly, to automatic calibration techniques employed in oximetry.

The arterial oxygen saturation and pulse rate of an individual may be of interest for a variety of reasons. For example, in the operating room up-to-date information regarding oxygen saturation can be used to signal changing physiological factors, the malfunction of anaesthesia equipment, or physician error. Similarly, in the intensive care unit, oxygen saturation information can be used to confirm the provision of proper patient ventilation and allow the patient to be withdrawn from a ventilator at an optimal rate.

In many applications, particularly including the operating room and intensive case unit, continual information regarding pulse rate and oxygen saturation is important if the presence of harmful physiological conditions is to be detected before a substantial risk to the patient is presented. A noninvasive technique is also desirable in many applications, for example, when a home health care nurse is performing a routine checkup, because it increases both operator convenience and patient comfort. Pulse transmittance oximetry is addressed to these problems and provides noninvasive, continual information about pulse rate and oxygen saturation. The information produced, however, is only useful when the operator can depend on its accuracy. The method and apparatus of the present invention are, therefore, directed to the improved accuracy of such information without undue cost.

As will be discussed in greater detail below, pulse transmittance oximetry basically involves measurement of the effect arterial blood in tissue has on the intensity of light passing therethrough. More particularly, the volume of blood in the tissue is a function of the arterial pulse, with a greater volume present at systole, and a lesser volume present at diastole. Because blood absorbs some of the light passing through the tissue, the intensity of the light emerging from the tissue is inversely proportional to the volume of blood in the tissue. Thus, the emergent light intensity will vary with the arterial pulse and can be used to indicate a patient's pulse rate. In addition, the absorption coefficient of oxyhemoglobin (hemoglobin combined with oxygen, $HbO_2$) is different from that of unoxygenated hemoglobin (Hb) for most wavelengths of light. For that reason, differences in the amount of light absorbed by the blood at two different wavelengths can be used to indicate the hemoglobin oxygen saturation, % $SaO_2$ (OS), which equals $([HbO_2]/([Hb]+[HbO_2]))\times 100\%$. Thus, measurement of the amount of light transmitted through, for example, a finger can be used to determine both the patient's pulse rate and hemoglobin oxygen saturation.

As will be appreciated, the intensity of light transmitted through a finger is a function of the absorption coefficient of both "fixed" components, such as bone, tissue, skin, and hair, as well as "variable" components, such as the volume of blood in the tissue. The intensity of light transmitted through the tissue, when expressed as a function of time, is often said to include a baseline component, which varies slowly with time and represents the effect of the fixed components on the light, as well as a periodic pulsatile component, which varies more rapidly with time and represents the effect that changing tissue blood volume has on the light. Because the attenuation produced by the fixed tissue components does not contain information about pulse rate and arterial oxygen saturation, the pulsatile signal is of primary interest. In that regard, many of the prior art transmittance oximetry techniques eliminate the so-called "DC" baseline component from the signal analyzed.

For example, in U.S. Pat. No. 2,706,927 (Wood) measurements of light absorption at two wavelengths are taken under a "bloodless" condition and a "normal" condition. In the bloodless condition, as much blood as possible is squeezed from the tissue being analyzed. Then, light at both wavelengths is transmitted through the tissue and absorption measurements made. These measurements indicate the effect that all nonblood tissue components have on the light. When normal blood flow has been restored to the tissue, a second set of measurements is made that indicates the influence of both the blood and nonblood components. The difference in light absorption between the two conditions is then used to determine the average oxygen saturation of the tissue, including the effects of both arterial and venous blood. As will be readily apparent, this process basically eliminates the DC, nonblood component from the signal that the oxygen saturation is extracted from.

For a number of reasons, however, the Wood method fails to provide the necessary accuracy. For example, a true bloodless condition is not practical to obtain. In addition, efforts to obtain a bloodless condition, such as by squeezing the tissue, may result in a different light transmission path for the two conditions. In addition to problems with accuracy, the Wood approach is both inconvenient and time consuming.

A more refined approach to pulse transmittance oximetry is disclosed in U.S. Pat. No. 4,167,331 (Nielsen). The disclosed oximeter is based upon the principle that the absorption of light by a material is directly proportional to the logarithm of the light intensity after having been attenuated by the absorber, as derived from the Beer-Lambert law. The oximeter employs light-emitting diodes (LEDs) to produce light at red and infrared wavelengths for transmission through tissue. A photosensitive device responds to the light produced by the LEDs, after it has been attenuated by the tissue, and produces an output current. That output current is amplified by a logarithmic amplifier to produce a signal having AC and DC components and containing information about the intensity of light transmitted at both wavelengths. Sample-and-hold circuits demodulate the red and infrared wavelength signals. The DC components of each signal are then blocked by a series of bandpass amplifier and capacitors, eliminating the effect of the fixed absorptive components from the signal. The resultant AC signal components are unaffected by fixed absorption components, such as hair, bone, tissue, skin. An average value of each AC signal is then produced. The ratio of the two averages is then used to determine the oxygen saturation from empirically determined values associated with the ratio. The AC components are also used to determine the pulse rate.

Another reference addressed to pulse transmittance oximetry is U.S. Pat. No. 4,407,290 (Wilker). In that reference, light pulses produced by LEDs at two different wavelengths are applied to, for example, an earlobe. A sensor responds to the light transmitted through the earlobe, producing a signal for each wavelength having a DC and AC component resulting from the presence of constant and pulsatile absorptive components in the earlobe. A normalization circuit employs feedback to scale both signals so that the DC nonpulsatile components of each are equal and the offset voltages removed. Decoders separate the two signals, so controlled, into channels A and B where the DC component is removed from each. The remaining AC components of the signals are amplified and combined at a multiplexer prior to analog-to-digital (A/D) conversion. Oxygen saturation is determined by a digital processor in accordance with the following relationship:

$$OS = \frac{X_1 R(\lambda_1) + X_2 R(\lambda_2)}{X_3 R(\lambda_1) + X_4 R(\lambda_2)}$$

wherein empirically derived data for the constants $X_1$, $X_2$, $X_3$ and $X_4$ is stored in the processor.

European Patent Application No. 83304939.8 (New, Jr. et al.) discloses an additional pulse transmittance oximeter. Two LEDs expose a body member, for example, a finger, to light having red and infrared wavelengths, with each LED having a one-in-four duty cycle. A detector produces a signal in response that is then split into two channels. The one-in-four duty cycle allows negatively amplified noise signals to be integrated with positively amplified signals including the detector response and noise, thereby eliminating the effect of noise on the signal produced. The resultant signals include a substantially constant DC component and an AC component. To improve the accuracy of a subsequent analog-to-digital (A/D) conversion, a fixed DC value is subtracted from the signal prior to the conversion. This level is then added back in by a microprocessor after the conversion. Logarithmic analysis is avoided by the microprocessor in the following manner. For each wavelength of light transmitted through the finger, a quotient of the AC component over the constant component is determined. The ratio of the two quotients is then determined and fitted to a curve of independently derived oxygen saturations. To compensate for the different transmission characteristics of different patient's fingers, an adjustable drive source for the LEDs is provided.

In European Patent Application 83304940.6 (New et al.), a calibrated oximeter probe is disclosed. That probe includes a coding resistor or coding connector used to identify the particular combination of wavelengths of light emitted by the two LEDs contained thereon. Oximeter circuitry then senses the code of the resistor or connector to determine the wavelengths of light emitted by the LEDs. In this manner, the effect that different wavelengths have on the oxygen saturation computations can be compensated for. The basis upon which oxygen saturation is measured involves the determination of the quotient of the pulsatile component over the constant component of light transmitted at each wavelength. The ratio of the quotients for the two wavelengths is then fitted to a curve of independently derived oxygen saturations. Outputs include pulse rate and oxygen saturation.

Even with the calibration techniques of New, Jr. et al. employed, however, the wavelengths of light emitted by the LEDs may change in a manner that the oximeter circuitry is usable to detect. As will be appreciated, such variations can significantly affect the accuracy of the oxygen saturation measurements. The disclosed invention is directed to the provision of more complete information about the actual wavelengths of the light emitted and, hence, the production of more accurate oxygen saturation measurements.

SUMMARY OF THE INVENTION

The present invention discloses a method of determining the oxygen saturation of arterial blood flowing in tissue. The method includes an initial step in which the tissue is exposed to light from two sources at separate temperature-dependent wavelengths. An indication of the temperature of the sources is produced, as are signals produced in response to the exposure of the tissue to the light at the separate temperature-dependent wavelengths. A preliminary indication of the oxygen saturation is then produced from the signals. A comparison of independently derived oxygen saturations with a continuum of such preliminary indications of oxygen saturation is then selected in accordance with the indication of the temperature of the sources earlier produced. From this comparison, the actual oxygen saturation corresponding to the preliminary indication previously obtained is produced.

In accordance with a particular aspect of the invention, an indication of the separate temperature-dependent wavelengths of light emitted by the sources at a reference temperature is produced. This indication is used to further aid in the selection of the appropriate comparison of independently derived oxygen saturations to the preliminary indications of oxygen saturation.

In accordance with a further aspect of the invention, an oximeter is disclosed that employs the foregoing method to determine the oxygen saturation of arterial blood flowing in tissue. The oximeter includes first and second light sources that illuminate the tissue with light at separate temperature-dependent wavelengths. The oximeter also includes a temperature detector that produces an indication of the temperature of the light sources. Signal that are proportional to the intensity of light received from the tissue at each of the temperature-dependent wavelengths are produced by a light detector and a processor analyzes the signals to produce a preliminary indication of the oxygen saturation of the blood. A selection circuit selects a particular comparison of oxygen saturations with the continuum of preliminary indications of the oxygen saturation in accordance with the indication of temperature received. Finally, a converter converts the preliminary indication of oxygen saturation into an oxygen saturation determination by reference to the comparison selected.

In accordance with additional aspects of the invention, a red optical filter filters the light received by the light detector. The signals produced by the light detector can, similarly, be amplified by a differential current-to-voltage amplifier before being analyzed by the processor. A sensor housing, having first and second elements, is employed to receive the tissue being analyzed and to define a light path between the light sources and the detector. A mirror, attached to the housing, is positioned between the light sources and detector and breaks the light path up into first and second segments at a predetermined angle with respect to each other. The two elements of the housing may pivot and be closably biased. In another arrangement, an apparatus is constructed in accordance with this invention independently of the light sources and light detector.

In accordance with another aspect of the invention, a sensor is disclosed for use with an oximeter to determine the oxygen saturation of arterial blood flowing in tissue. The sensor includes first and second light sources for illuminating the tissue with light at separate temperature-dependent wavelengths. A temperature indicator is also included to produce an indication of the temperature of the light sources. Signals are produced in response to the illumination of the tissue at each of the temperature-dependent wavelengths by a light detector.

BRIEF DESCRIPTION OF THE DRAWINGS

The invention can best be understood by reference to the following portion of the specification, taken in conjunction with the accompanying drawings in which:

FIG. 11 is an exploded view showing the sensor of FIG. 1 in greater detail;

FIG. 15 is a graphical representation of the possible ranges of I/O circuit output, showing the desired response to the I/O circuit and microcomputer at each of the various possible ranges;

FIG. 17 is a family of curves similar to the one illustrated in FIG. 7.

DETAILED DESCRIPTION

Figure 1:
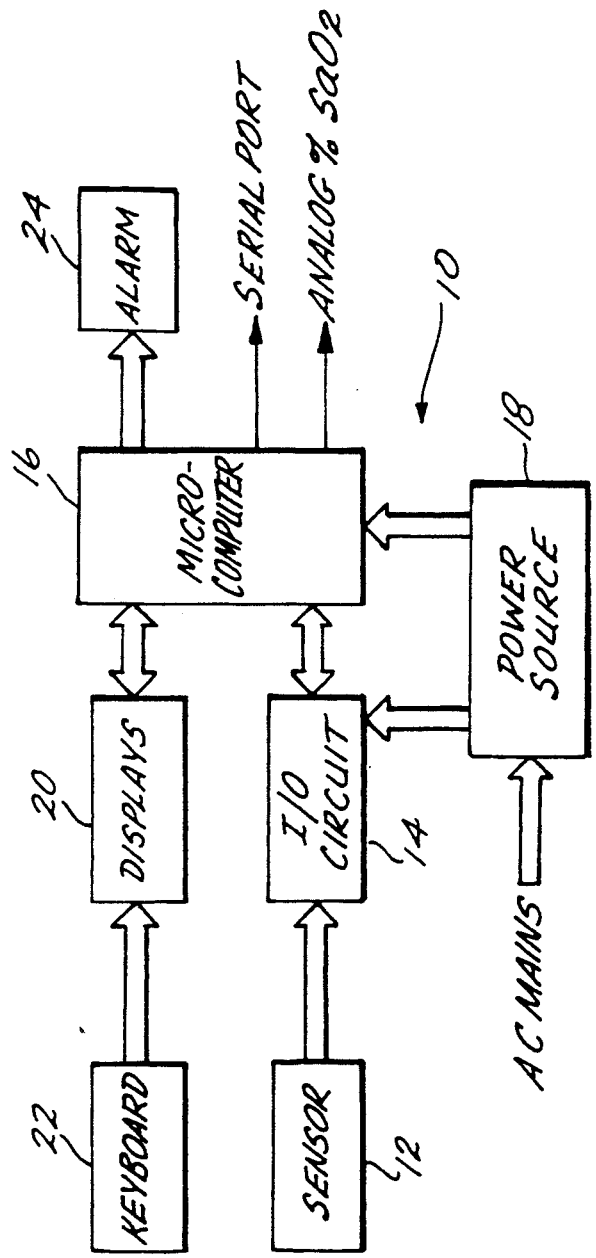
FIG. 1 is a block diagram of an oximeter including a sensor, input/output (I/O) circuit, microcomputer, alarm, displays, power supply, and keyboard.

Referring to the overall system block diagram shown in FIG. 1, a pulse transmittance oximeter 10 employing this invention includes a sensor 12, input/output (I/O) circuit 14, microcomputer 16, power source 18, display 20, keyboard 22 and alarm 24. Before discussing these elements in detail, however, an outline of the theoretical basis of pulse transmittance oximetry as practiced by the oximeter of FIG. 1 is provided.

An understanding of the relevant theory begins with a discussion of the Beer-Lambert law. This law governs the absorption of optical radiation by homogeneous absorbing media and can best be understood with reference to FIGS. 2 and 3 in the following manner.

Figure 2:
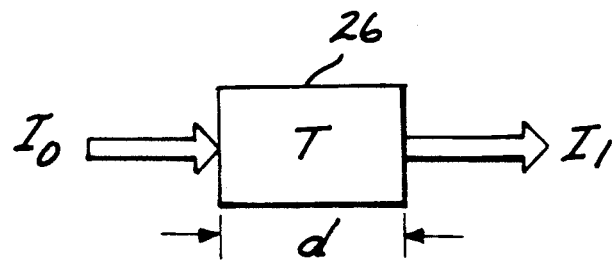
FIG. 2 is a block diagram illustrating the transmission of light through an absorptive medium.
Figure 3:
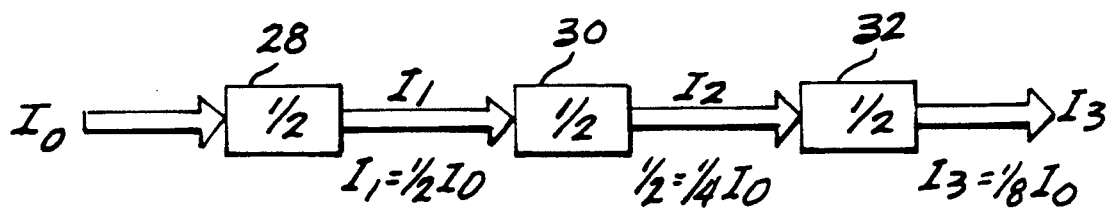
FIG. 3 is a block diagram illustrating the transmission of light through the absorptive medium of FIG. 2, wherein the medium is broken up into elemental components.

As shown in FIG. 2, incident light having an intensity $I_0$ impinges upon an absorptive medium 26. Medium 26 has a characteristic absorbance factor A that indicates the attenuating affect medium 26 has on the incident light. Similarly, a transmission factor T for the medium is defined as the reciprocal of the absorbance factor, 1/A. The intensity of the light $I_1$ emerging from medium 26 is less than $I_0$ and can be expressed functionally as the product $TI_0$. With medium 26 divided into a number of identical components, each of unit thickness (in the direction of light transmission) and the same transmission factor T, the effect of medium 26 on the incident light $I_0$ is as shown in FIG. 3.

There, medium 26 is illustrated as consisting of three components 28, 30, and 32. As will be appreciated, the intensity $I_1$ of the light emerging from component 28 is equal to the incident light intensity $I_0$ multiplied by the transmission factor T. Component 30 has a similar effect on light passing therethrough. Thus, because the light incident upon component 30 is equal to the product $TI_0$, the emergent light intensity $I_2$ is equal to the product $TI_1$ or $T^2I_0$. Component 32 has the same effect on light and, as shown in FIG. 3, the intensity of the emergent light $I_3$ for the entire medium 26 so modeled is equal to the product $TI_2$ or $T^3I_0$. If the thickness d of medium 26 is n unit lengths, it can be modeled as including n identical components of unit thickness. It will then be appreciated that the intensity of light emerging from medium 26 can be designated $I_n$ and the product is equal to $T^nI_0$. Expressed as a function of the absorbance constant A, $I_n$ can also be written as the product $(1/A^n)I_0$.

From the preceding discussion, it will be readily appreciated that the absorptive effect of medium 26 on the intensity of the incident light $I_0$ is one of exponential decay. Because A may be an inconvenient base to work with, $I_n$ can be rewritten as a function of a more convenient base, b, by recognizing that $A^n$ is equal to $b^{\alpha n}$, where $\alpha$ is the absorbance of medium 26 per unit length. The term $\alpha$ is frequently referred to as the extinction coefficient and is equal to $\log_b A$.

Figure 4:
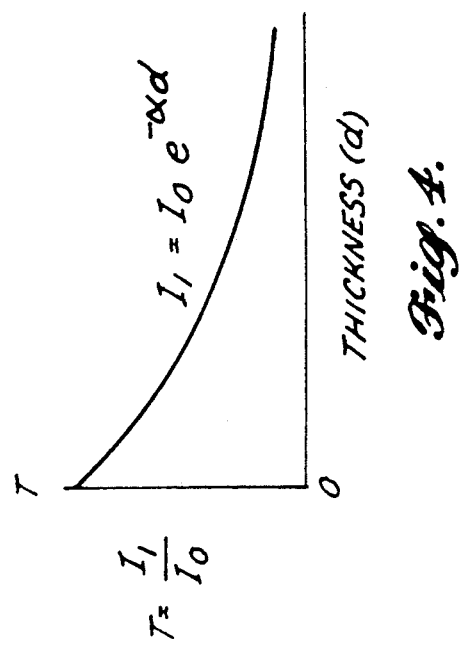
FIG. 4 is a graphical comparison of the incident light intensity to the emergent light intensity as modeled in FIG. 2.

Given the preceding discussion, it will be appreciated that the intensity of the light $I_n$ emerging from medium 26 can be expressed in base 10 as $I_0 10^{-\alpha_1 n}$, or in base e as $I_0 e^{-\alpha_2 n}$, where $\alpha_1$ and $\alpha_2$ are the appropriate relative extinction coefficients for base 10 and base e respectively. The effect that the thickness of medium 26 has on the emergent light intensity $I_n$ is graphically depicted in FIG. 4. If the light incident upon medium 26 is established as having unit intensity, FIG. 4 also represents the transmission factor T of the entire medium as a function of thickness.

The discussion above can be applied generally to the medium 26 shown in FIG. 2 to produce:

$$I_1 = I_0 e^{-\alpha d} \quad (1)$$

where $I_1$ is the emergent light intensity, $I_0$ is the incident light intensity, $\alpha$ is the absorbance coefficient of the medium per unit length, d is the thickness of the medium in unit lengths, and the exponential nature of the relationship ha arbitrarily been expressed in terms of base e. Equation (1) is commonly referred to as the Beer-Lambert law of exponential light decay through a homogeneous absorbing medium.

Figure 5:
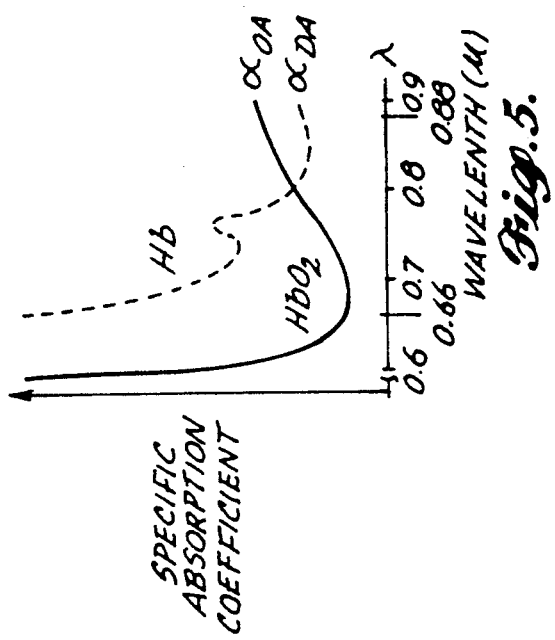
FIG. 5 is a graphical comparison of the specific absorption coefficients for oxygenated hemoglobin and deoxygenated hemoglobin as a function of the wavelength of light transmitted therethrough.

While the basic understanding of the Beer-Lambert law, a discussion of its application to the problems of pulse rate and hemoglobin oxygen saturation measurement is now presented. As shown in FIG. 5, the absorption coefficients for oxygenated and deoxygenated hemoglobin are different at every wavelength, except isobestic wavelengths. Thus, it will be appreciated that if a person's finger is exposed to incident light and the emergent light intensity measured, the difference in intensity between the two, which is the amount of light absorbed, contains information relating to the oxygenated hemoglobin content of the blood in the finger. The manner in which this information is extracted from the Beer-Lambert law is discussed below. In addition, it will be appreciated that the volume of blood contained within an individual's finger varies with the individual's arterial pulse. Thus, the thickness of the finger also varies slightly with each pulse, creating a changing path length for light transmitted through the finger. Because a longer lightpath allows additional light to be absorbed, time-dependent information relating to the difference between the incident and emergent light intensities can be used to determine the individual's pulse. The manner in which this information is extracted from the Beer-Lambert law is also discussed below.

As noted in the preceding paragraph, information about the incident and emergent intensities of light transmitted through a finger can be used to determine oxygen saturation and pulse rate. The theoretical basis for extracting the required information, however, is complicated by several problems. For example, the precise intensity of the incident light applied to the finger is not easily determined. Thus, it may be necessary to extract the required information independently of the intensity of the incident light. Further, because the charging volume of blood in the finger and, hence, thickness of the lightpath therethrough, are not excessively dependent upon the individual's pulse, it is desirable to eliminate the changing path length as a variable from the computations.

Figure 6:
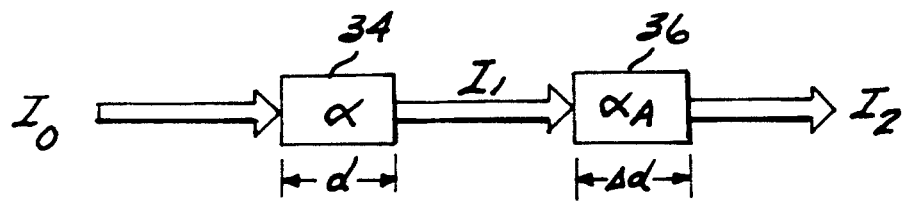
FIG. 6 is a block diagram illustrating the transmission of light through a block model of the components of a finger.

The manner in which the Beer-Lambert law is refined to eliminate the incident intensity and path lengths as variables is as follows. With reference to FIG. 6, a human finger is modeled by two components 34 and 36, in a manner similar to that shown in FIG. 3. Baseline component 34 models the unchanging absorptive elements of the finger. This component includes, for example, bone, tissue, skin, hair, and baseline venous and arterial blood and has a thickness designated d and an absorbance $\alpha$.

Pulsatile component 36 represents the changing absorptive portion of the finger, the arterial blood volume. As shown, the thickness of this component is designated $\Delta d$, representing the variable nature of the thickness, and the absorbance of this component is designated $\alpha_A$ representing the arterial blood absorbance.

As will be appreciated from the earlier analysis with respect to FIG. 3, the light $I_1$ emerging from component 34 can be written as a function of the incident light intensity $I_0$ as follows:

$$I_1 = I_0 e^{-\alpha d} \quad (2)$$

Likewise, the intensity of light $I_2$ emerging from component 36 is a function of its incident light intensity $I_1$, and:

$$I_2 = I_1 e^{-\alpha_A \Delta d} \quad (3)$$

Substitution of the expression for $I_1$ developed in equation (2) for that used in equation (3), when simplified, results in the following expression for the intensity $I_2$ of light emerging from the finger as a function of the intensity of light $I_0$ incident upon the finger:

$$I_2 = I_0 e^{-[\alpha d + \alpha_A \Delta d]} \quad (4)$$

Because our interest lies in the effect of the light produced by the arterial blood volume, the relationship between $I_2$ and $I_1$ is of particular interest. Defining the change in the transmission produced by the arterial component 36 as $T_{\Delta A}$, we have:

$$T_{\Delta A} = \frac{I_2}{I_1} \quad (5)$$

Substituting the expressions for $I_1$ and $I_2$ obtained in equations (2) and (3), respectively, equation (5) becomes:

$$T_{\Delta A} = \frac{I_0 e^{-[\alpha d + \alpha_A \Delta d]}}{I_0 e^{-\alpha d}} \quad (6)$$

It will be appreciated that the $I_0$ term can be cancelled from both the numerator and denominator of equation (6), thereby eliminating the input light intensity as a variable in the equation. With equation (6) fully simplified, the change in arterial transmission can be expressed as:

$$T_{\Delta A} = e^{-\alpha_A \Delta d} \quad (7)$$

A device employing this principle of operation is effectively self-calibrating, being independent of the incident light intensity $I_0$.

At this point, a consideration of equation (7) reveals that the changing thickness of the finger, $\Delta d$, produced by the changing arterial blood volume still remains as a variable. The $\Delta d$ variable is eliminated in the following manner. For convenience of expression, the logarithms of terms in equation (7) are produced with respect to the same base originally employed in equation (1). Thus, equation (7) becomes:

$$\ln T_{\Delta A} = \ln(e^{-\alpha_A \Delta d}) = -\alpha_A \Delta d \quad (8)$$

A preferred technique for eliminating the $\Delta d$ variable utilizes information drawn from the change in arterial transmission experienced at two wavelengths.

The particular wavelengths selected are determined in part by consideration of a more complete expression of the arterial absorbance $\alpha_A$:

$$\alpha_A = (\alpha_{OA})/(OS) - (\alpha_{DA})(1 - OS) \quad (9)$$

where $\alpha_{OA}$ is the oxygenated arterial absorbance, $\alpha_{DA}$ is the deoxygenated arterial absorbance, and OS is the hemoglobin oxygen saturation of the arterial blood volume. As will be appreciated from FIG. 5, $\alpha_{OA}$ and $\alpha_{DA}$ are substantially unequal at all light wavelengths in the visible-red and near-infrared wavelength regions except for an isobestic wavelength occurring at approximately 805 nanometers. With an arterial oxygen saturation OS of approximately 90 percent, it will be appreciated from equation (9) that the arterial absorbance $\alpha_A$ is 90 percent attributable to the oxygenated arterial absorbance $\alpha_{OA}$ and 10 percent attributable to the deoxygenated arterial absorbance $\alpha_{DA}$. At the isobestic wavelength, the relative contribution of these two coefficients to the arterial absorbance $\alpha_A$ is of minimal significance in that both $\alpha_{OA}$ and $\alpha_{DA}$ are equal. Thus, a wavelength roughly approximately the isobestic wavelength of the curves illustrated in FIG. 5 is a convenient one for use in eliminating the change in finger thickness $\Delta d$ attributable to arterial blood flow.

A second wavelength is selected at a distance from the approximately isobestic wavelength that is sufficient to allow the two signals to be easily distinguished. In addition, the relative difference of the oxygenated and deoxygenated arterial absorbances at this wavelength is more pronounced. In light of the foregoing considerations, it is generally preferred that the two wavelengths selected fall within the red and infrared regions of the electromagnetic spectrum.

The foregoing information, when combined with equation (8) is used to produce the following ratio:

$$\frac{\ln T_{\Delta AR}}{\ln T_{\Delta AIR}} = \frac{-\alpha_A \Delta d @ \lambda_R}{-\alpha_A \Delta d @ \lambda_{IR}} \quad (10)$$

where $T_{\Delta AR}$ equals the change in arterial transmission of light at the red wavelength $\lambda_R$ and $T_{\Delta AIR}$ is the change in arterial transmission at the infrared wavelength $\lambda_{IR}$. It will be appreciated that if two sources are positioned at substantially the same location on the finger, the length of the lightpath through the finger is substantially the same for the light emitted by each. Thus, the change in the lightpath resulting from arterial blood flow, $\Delta d$, is substantially the same for both the red and infrared wavelength sources. For that reason, the $\Delta d$ term in the numerator and denominator of the right-hand side of equation (10) cancel, producing:

$$\frac{\ln T_{\Delta AR}}{\ln T_{\Delta AIR}} = \frac{\alpha_A @ \lambda_R}{\alpha_A @ \lambda_{IR}} \quad (11)$$

As will be appreciated, equation (11) is independent of both the incident light intensity $I_0$ and the change in finger thickness $\Delta d$ attributable to arterial blood flow. The foregoing derivations form the theoretical basis of pulse oximetry measurement. Because of the complexity of the physiological process, however, the ratio indicated in equation (11) does not directly provide an accurate measurement of oxygen saturation. The correlation between the ratio of equation (11) and actual arterial blood gas measurements is, therefore, relied on to produce an indication of the oxygen saturation. Thus, if the ratio of the arterial absorbance at the red and infrared wavelengths can be determined, the oxygen saturation of the arterial blood flow can be extracted from independently derived, empirical calibration curves in a manner independent of $I_0$ and $\Delta d$.

For simplicity, a measured ratio $R_{OS}$ is defined from equation (11) as:

$$\text{Ratio} = R_{OS} = \frac{\alpha_A @ \lambda_R}{\alpha_A @ \lambda_{IR}} \quad (12)$$

Figure 7:
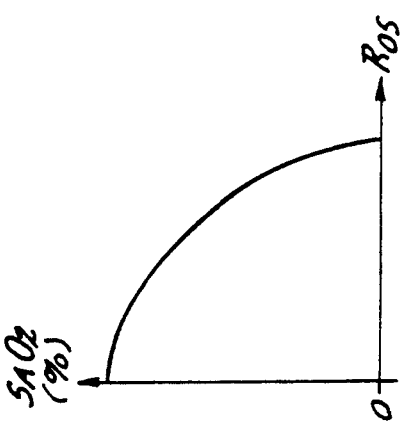
FIG. 7 is a graphical comparison of independently derived oxygen saturation measurements with a variable that is measured by the oximeter.

It is this measured value for $R_{OS}$ that is plotted on the x-axis of independently derived oxygen saturation curves, as shown in FIG. 7 and discussed in greater detail below, with the hemoglobin oxygen saturation being referenced on the y-axis.

Figure 9:
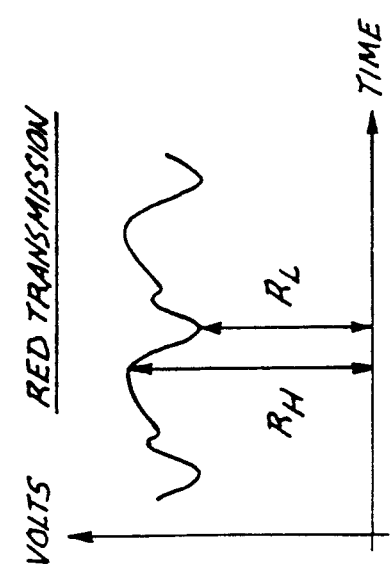
FIG. 9 is a graphical plot as a function of time of the transmittance of light at the red wavelength through the finger.
Figure 8:
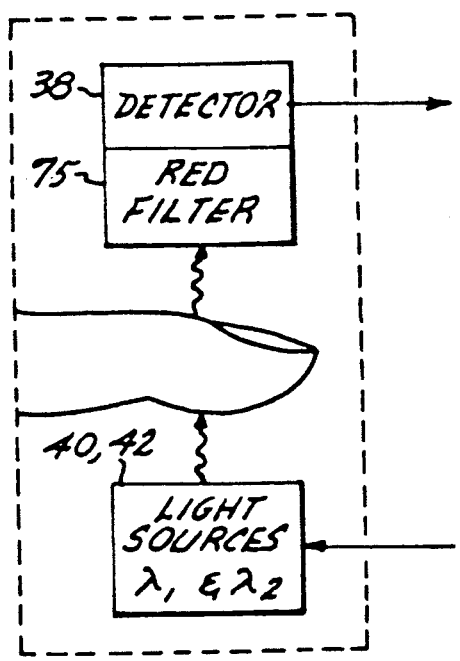
FIG. 8 is a schematic illustration of the transmission of light at two wavelengths through a finger in accordance with the invention.

Measurement of the arterial absorbances at both wavelengths is performed in the following manner. As shown in FIG. 8, a detector 38 placed on the side of a finger opposite red and infrared wavelength light sources 40 and 42 receives light at both wavelengths transmitted through the finger. As shown in FIG. 9, the received red wavelength light intensity, plotted as a function of time, varies with each pulse, and has high and low values $R_H$ and $R_L$, respectively. $R_L$ occurs substantially at systole, when arterial blood volume is at its greatest; while $R_H$ occurs substantially at diastole, when the arterial blood volume is lowest. From the earlier discussion of the exponential light decay through homogeneous media, it will be appreciated that:

$$R_L = I_0 e^{-[\alpha d + \alpha_A \Delta d]} @ \lambda_R \quad (13)$$

Similarly:

$$R_H = I_0 e^{-\alpha d} @ \lambda_R \quad (14)$$

Taking the ratio of equations (13) and (14) and simplifying, we have:

$$\frac{R_L}{R_H} = \frac{I_0 e^{-[\alpha d + \alpha_A \Delta d]}}{I_0 e^{-\alpha d}} @ \lambda_R = e^{-\alpha_A \Delta d} @ \lambda_R \quad (15)$$

Taking the logarithm of both sides of equation (15) produces:

$$\ln(R_L/R_H) = \ln(e^{-\alpha_A \Delta d}) @ \lambda_R = -\alpha_A \Delta d @ \lambda_R \quad (16)$$

As will be readily appreciated, similar expression can be produced for the signals representative of the infrared wavelength light received by detector 38. Thus, the minimum light intensity passing through the finger at the infrared wavelength can be written:

$$IR_L = I_0 e^{-[\alpha d + \alpha_A \Delta d]} @ \lambda_{IR} \quad (17)$$

Similarly, the maximum light intensity emerging from the finger at the infrared wavelength can be expressed as:

$$IR_H = I_0 e^{-\alpha d} @ IR \quad (18)$$

The ratio of the terms in equations (17) and (18) can be expressed as:

$$\frac{IR_L}{IR_H} = \frac{I_0 e^{-[\alpha d + \alpha_A \Delta d]}}{I_0 e^{-\alpha d}} @ \lambda_{IR} = e^{-\alpha_A \Delta d} @ \lambda_{IR} \quad (19)$$

Use of logarithms simplifies equation (19) to:

$$\ln(IR_L/IR_H) = \ln(e^{-\alpha_A \Delta d}) @ \lambda_{IR} = -\alpha_A \Delta d @ \lambda_{IR} \quad (20)$$

The ratiometric combination of equations (16) and (20) yields:

$$\frac{\ln(R_L/R_H)}{\ln(IR_L/IR_H)} = \frac{-a_A \Delta d \ @ \ \lambda_R}{-a_A \Delta d \ @ \ \lambda_{IR}} \qquad (21)$$

Because the Δterm in the numerator and denominator of the right-hand side of equation (21) cancel, as do the negative signs before each term, it will be appreciated that equation (21) when combined with equation (12) yields:

$$\text{Ratio} = R_{OS} = \frac{a_A \ @ \ \lambda_R}{a_A \ @ \ \lambda_{IR}} = \frac{\ln(R_L/R_H)}{\ln(IR_L/IR_H)} = \frac{\ln(R_H/R_L)}{\ln(IR_H/IR_L)} \qquad (22)$$

Thus, by measuring the minimum and maximum emergent light intensities at both the red and infrared wavelengths ($R_L$, $R_H$, $IR_L$, $IR_H$), a value for the term $R_{OS}$ can be computed. From this, empirically derived calibration curves similar to that shown in FIG. 7 can be used to determine the oxygen saturation as described in greater detail in conjunction with the discussion of the various components of oximeter 10 that follows. As will be appreciated, the determination of oxygen saturation in this manner differs from prior art techniques, such as that disclosed by Wilker, by performing measurements based upon both the baseline and pulsatile components of the signals.

The first component of oximeter 10 to be discussed is sensor 12. The function of sensor 12 is substantially to provide the desired orientation of light sources 40 and 42, for example, light-emitting diodes (LEDs), and light detector 38 with respect to a suitable portion of a patient's body. For example, the sensor must align LEDs 40 and 42 with detector 38 in a manner such that the path of light from each LED to the detector 38 is substantially the same distance. In addition, the path must traverse a portion of the patient's body through which a usable amount of light is passed, for example, a finger, toe, earlobe, or the nasal septum. Because changes in the lightpath can s significantly affect the readings taken, as noted above, the sensor must maintain the position of LEDs 40 and 42 and detector 38 with respect to the transmission path through the patient's skin at all times. Otherwise, signal fluctuations known as motion-artifact may be produced. In addition, the sensor should apply only insubstantial pressure to the patient's skin and underlying tissue. Otherwise, normal arterial blood flow upon which the pulse oximeter relies for accurate operation, may be disrupted. Finally, the sensor should be quickly attachable to the patient and should cause no discomfort.

The details of the sensor 12, constructed to satisfy the foregoing requirements, are shown in FIG. 11. Sensor 12 includes a connector 44, cable 46, and sensor optical component assembly 48 and, in the arrangement shown, is for use with the finger of a patient. Connector 44 is a male, 9-pin plug that engages a mating female receptacle provided on the oximeter housing (not shown), thereby providing attachment of sensor 12 to the oximeter 10. The connector 44 is preferably custom molded to cable 46 for durability.

Cable 46 is a six-conductor, shielded cable having one shielded, twisted-wire pair and four single wires. The twisted-wire pair conducts the signal from the detector 38 in sensor assembly 48 to I/O circuit 14. Two of the single wires conduct power to the LEDs 40 and 42. The remaining two wires, in conjunction with the common shield, are connected to a temperature sensor 50 and coding resistor 52 included in, for example, the sensor assembly 48.

Addressing now the detailed construction of sensor assembly 48, a sensor housing is defined by base 54 and cover 56. Base 54 and cover 56 are made of an opaque plastic that shields detector 38 from the influence of the ambient light that sensor assembly 48 is exposed to. The cover 56 is pivotal about hubs 58 provided on one end of the base 54. This hinged arrangement of base 54 and cover 56 allows the housing to accommodate a range of adult finger sizes.

Upper and lower cushions 60 and 62 are provided near the open end of the housing on cover 56 and base 54, respectively, and form opposing, cup-shaped resilient surfaces for contacting the finger. A torsion spring 64 tends to close the hinged base 54 and cover 56, thereby applying a slight pressure to the patient's finger through the cushions 60 and 62. In this manner, a comfortable attachment of sensor assembly 48 to the finger is provided. In addition, sensor assembly 48 will not slip significantly with respect to the finger, thus reducing the likelihood that motion affects will affect the oxygen saturation and pulse rate determined. Light from the open end of sensor assembly 48 is also substantially blocked by the engagement of upper and lower cushions 60 and 62 with the patient's finger.

LEDs 40 and 42 are mounted on a lower retainer 66 attached to base 54. A shallow depression is provided in the upper surface of retainer 66 for receiving the anterior side of the patient's finger. A lens 68 is provided in the lower retainer 66 and conforms to the shape of the depression therein. Lens 68 allows light from LEDs 40 and 42, when reflected off mirror 74, to impinge upon the patient's finger in a direction substantially perpendicular to the longitudinal axis of the finger when extended. An upper retainer 70 is affixed to the cover 56 and has a lower surface provided with a depression for receiving the dorsal side of the patient's finger. A lens 72 provided in the upper retainer 70 opposite the lower retain lens 68, allows light passing through the finger to improve upon detector 38 for conversion into an electrical signal. Mirror 74 is held in place by the lower retainer 66 at an angle, preferably 45 degrees, with respect to the lightpath. This arrangement allows sensor assembly 48 to be more compact when viewed in the direction of the lightpath through the finger. The detector 38 is held in place by the upper retainer 70. In a preferred arrangement, the temperature sensor 50 is also provided on the lower retainer 70.

As will be appreciated from the brief discussion of oximetry theory provided above, the wavelengths of light emitted by the particular LEDs 40 and 42 selected affect the measurement of oxygen saturation. Therefore, the wavelengths of light emitted by each LED must be known and the LEDs segregated by their peak emission wavelength prior to assembly into the sensor. More particularly, LEDs 40 and 42, which emit light at red and infrared wavelengths, respectively, are segregated by their pack wavelengths at a standard ambient temperature into appropriate predetermined incremental subsets of an appropriate predetermined given range of wavelengths. A two-dimensional matrix is then formed, with, for example, the rows including the various visible-red wavelength incremental subsets and the columns indicating the various near-infrared wavelength incremental subsets. Each position in the matrix has a particular coding resistor value assigned thereto. In this manner, the particular wavelength combination of LEDs 40 and 42 used in the senor is identified by a coding resistor 52 located, for example, adjacent the LEDs. With LEDs 40 and 42 each arranged into groups having defined wavelength ranges, different coding resistors 52 can be used to distinctly identify every possible combination of LEDs on sensor 12.

A current provided to the sensor 12 allows microcomputer 16 to determine the resistance of the coding resistor 52 by measuring the voltage drop across it. Thus, the particular combination of LEDs 40 and 42 employed in sensor 12 can be determined. Microcomputer 16 can then make the necessary adjustments to the determination of oxygen saturation, as discussed in greater detail below.

Because the wavelengths of light emitted by LEDs 40 and 42 influence the determination of oxygen saturation, accurate measurements require that the effect of temperature on the wavelengths also be compensated. As noted previously, a temperature sensor 50, for example, Thomson CSF LM335A, is employed to produce a signal that indicates the temperature of sensor assembly 48. As described in greater detail below, this signal, when combined with information about the coding resistor 52 value, allows microcomputer 16 to accurately determine the wavelengths of the light emitted by LEDs 40 and 42 and subsequently produce an accurate determination of oxygen saturation.

In a preferred embodiment of the invention, a red optical filter 76 interrupts the lightpath between the LEDS 40 and 42 and the detector 38. Preferably, red filter 76 is a Kodak No. 29 wratten gel filter. Its function is to minimize the influence of fluorescent light flicker on the oxygen saturation determination made. As will be appreciated, although the opaqueness of base 54 and cover 56 blocks a significant portion of the ambient light, some ambient light may still reach detector 38. Light from the sun and incandescent lamps is substantially continuous. Fluorescent lighting, on the other hand, includes alternating energized and deenergized intervals that form a visually imperceptible flicker. The frequency of the fluorescent light flicker is such that it might influence the signal produced by detector 38 in response to light received from LED 40 at the red wavelength. Thus, the red optical filter 76 is placed over the detector 38 and filters out most fluorescent light present, eliminating the effect its flicker might have on the oxygen saturation determination made.

Figure 12:
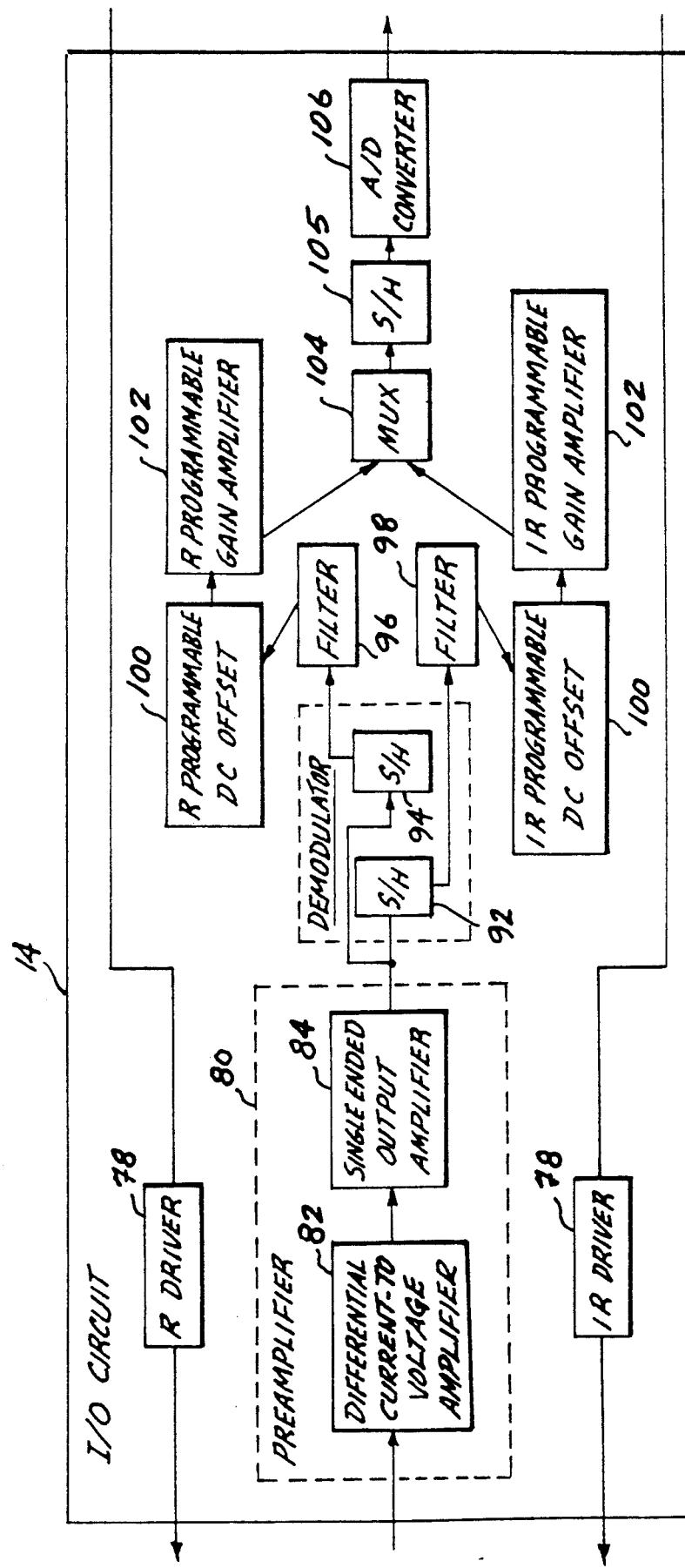
FIG. 12 is a more detailed schematic of the I/O circuit illustrated in the system of FIG. 1.

LEDs 40 and 42 are supplied with current by transistor drivers 78 located in the I/O circuit 14, as shown in FIG. 12. Drivers 78 are controlled by microcomputer 16 to produce current pulses at a 960 Hz repetition rate. The duration of each pulse is 70 microseconds and a pulse is supplied to the red wavelength LED 40 first and then to the infrared wavelength LED 42. The voltage drop across scaling resistors in the drivers 78 allows the magnitude of the current pulses to be determined and, thus, maintained in a manner described in greater detail below. LEDs 40 and 42 respond to the current pulses by producing corresponding light pulses transmitted through the finger to detector 38. Detector 38, in turn, produces a signal that includes information about the pulsatile response of the finger to the red and infrared wavelength light, intermixed at the 960 Hz LED pulse repetition rate.

Figure 13:
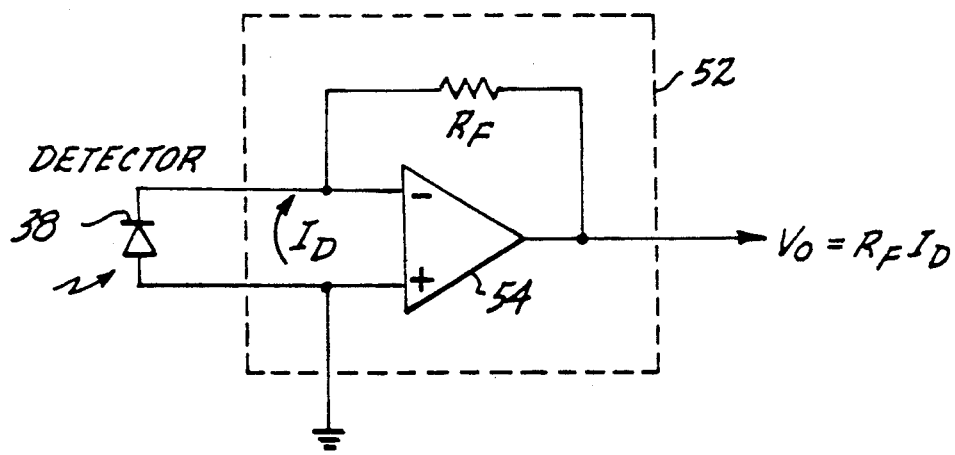
FIG. 13 is a schematic diagram of a conventional current-to-voltage amplifier circuit.

At the I/O circuit 14, the signal from detector 38 is received by a preamplifier 80. In a preferred embodiment, preamplifier 80 includes a differential current-to-voltage amplifier 82 and a single-ended output amplifier 84. To understand the advantages of using the differential amplifier 80, it may first be helpful to consider the operation of a conventional current-to-voltage amplifier as shown in FIG. 13. As shown, a current-to-voltage amplifier 86 is substantially comprised of an operational amplifier 88 and gain determination resistor $R_F$. With a detector 38 connected to the inputs of the amplifier as shown, a current $I_D$ is input to the amplifier upon the detection of suitable wavelength light. The output of amplifier 88 is designated $V_0$ and, as will be appreciated, is equal to the product of the detector current $I_D$ and the gain determination resistor $R_F$. The primary problem with such a construction is that it also amplifies the external interference noise produced, making the signal extracted less accurate.

Figure 14:
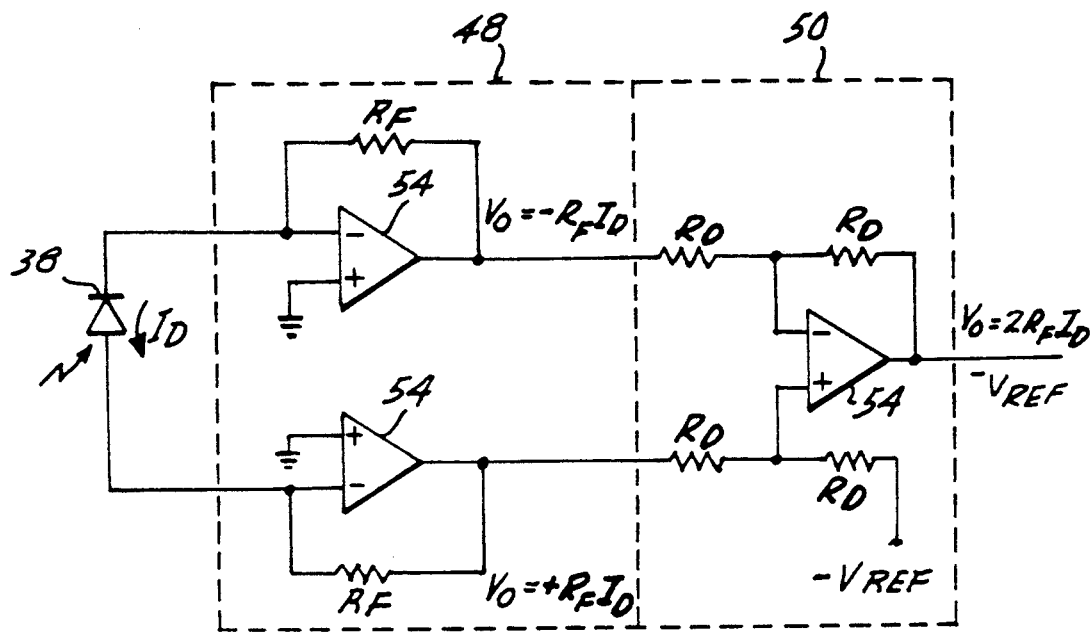
FIG. 14 is a schematic diagram of a differential current-to-voltage preamplifier circuit included in the I/O circuit of FIG. 1.

Adoption of the different current-to-voltage amplifier 82, when combined with the single-ended output amplifier 84 as shown in FIG. 14, however, eliminates this problem. As shown, the differential amplifier 82 produces positive and negative versions of the output, the absolute value of each version being equal to the product of the gain determination resistance $R_F$ and the detector current $I_D$. These outputs are then supplied to the single-ended output amplifier 84, which provides unity gain, thus producing an output signal having a magnitude that is twice that of the inputs. An advantage of this arrangement is that external interference noise is cancelled at the single-ended output amplifier 84 by the opposing signs of the two differential transimpedance amplifier outputs. In addition, twice the signal is produced with the current noise only increasing by a magnitude of 1.414. Therefore, an improved signal-to-noise ratio results.

Figure 10:
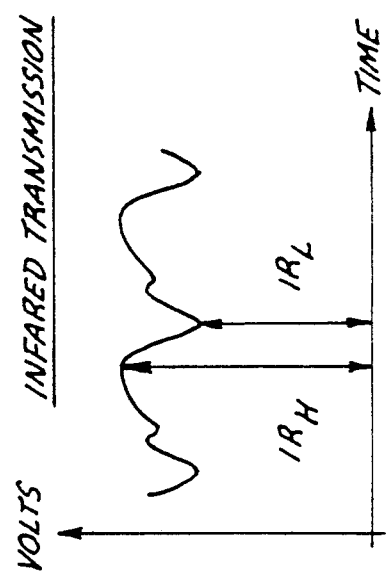
FIG. 10 is a graphical plot as a function of time of the transmission of infrared light through the finger.

At this point, the mixed signal indicative of the red and infrared wavelength responses of detector 38 has been amplified and is input to a demodulator 90 to extract the red pulsatile and infrared pulsatile waveforms shown in FIGS. 9 and 10. In a preferred arrangement, the demodulator 90 includes a sample-and-hold (S/H) circuit 94 that responds to the detector signal produced in response to red wavelength light and a sample-and-hold (S/H) circuit 92 that responds to the infrared wavelength response of detector 38. The timing of circuits 92 and 94 is controlled so that each circuit samples the signal input to demodulator 90 during the portion of the signal corresponding to the wavelength to which it responds. In this manner, two signals are reconstructed from the single input to demodulator 90. As noted above, these signals correspond to the red pulsatile signal and infrared pulsatile signals shown in FIGS. 9 and 10.

To remove high-frequency noise from the outputs of circuits 92 and 94, they are input to lowpass filters 96 and 98. In a preferred embodiment, the "red" lowpass filter 96 and "infrared" lowpass filter 98 each include two stages. The first stage of each filter utilizes a fifth-order, monolithic integrated circuit switched capacitor filter because of its low cost, relatively small physical size, and accuracy. Since both the "red" and "infrared" signals pass through nearly identical first-stage filters due to monolithic integrated-circuit matching, their gain and phase frequency responses are matched. The second stage of each filter is a second-order Bessel filter having a slightly higher roll-off frequency than the first stage. This insures that the first-stage filter is the dominant filter of the two-stage combination, providing the desired filtering accuracy. The second stage then filters the switching noise from the first-stage output.

The filtered red and infrared pulsatile signals are next prepared for conversion and transmission of the microcomputer 16. As will be discussed in greater detail below, this process involves the use of a programmable DC subtractor or offset 100 followed by a programmable gain amplifier 102 having a gain range from approximately one to 256. The appropriately processed signals are combined at multiplex 104, sampled and held, and converted to digital form by A/D converter 106 for transmission to microcomputer 16.

Before a more complete discussion of the operation of programmable subtractor 100, programmable gain amplifier 102, multiplexer 104, sample-and-hold circuit 105, and A/D converter 106 is provided, several details regarding the signals to be transferred to microcomputer 16 should be noted. For example, as shown in FIGS. 9 and 10, the signal produced by detector 38 in response to light at each wavelength includes components that, for convenience, are termed baseline and pulsatile. The baseline component approximates the intensity of light received at detector 38 when only the "fixed" nonpulsatile absorptive component is present in the finger. This component of the signal is relatively constant over short intervals but does vary with nonpulsatile physiological changes or system changes, such as movement of sensor 12 on the finger. Over a relatively long interval this baseline component may vary significantly. As will be appreciated, the magnitude of the baseline component at a given point in time is substantially equal to the level identified in FIG. 9 as $R_H$. For convenience, however, the baseline component may be thought of as the level indicated by $R_L$, with the pulsatile component varying between the values for $R_H$ and $R_L$ over a given pulse. That pulsatile component is attributable to light transmission changes through the finger resulting from blood volume changes in the finger during a cardiac pulse. Typically, the pulsatile component may be relatively small in comparison to the baseline component and is shown out of proportion in FIGS. 9 and 10.

The determination of $R_{OS}$ in accordance with equation (22) requires accurately measured values for both the baseline and pulsatile signal components. Because the pulsatile components are smaller, however, greater case must be exercised with respect to the measurement of these components. As will be readily appreciated, if the entire signal shown in FIGS. 9 and 10, including the baseline and pulsatile components, was amplified and converted to a digital format for use by microcomputer 16, a great deal of the accuracy of the conversion would be wasted because a substantial portion of the resolution would be used to measure the baseline component. For example, with an A/D converter employed having an input range of between $+10$ and $-10$ volts, a signal having a baseline component referenced to $-10$ volts that is four times that of the pulsatile component can be amplified until the baseline component is represented by a 16-volt difference and the pulsatile signal represented by a 4-volt difference. With a 12-bit A/D converter 106, the total signal can be resolved into 4096 components. Therefore, the number of incremental levels representing the pulsatile signal would be approximately 819. If, on the other hand, the baseline component is removed prior to the conversion, the gained pulsatile signal could be resolved into 4096 intervals, substantially improving accuracy.

The disclosed invention employs this technique, as the first half of a construction-reconstruction process controlled by microcomputer 16. Accordingly, an input signal received from each filter 96 and 98 includes both the AC and DC components discussed above. The programmable subtractors 100 remove a substantial offset portion of the baseline component of each signal and the programmable gain amplifiers 102 gain-up the remaining signal for conversion by A/D converter 106. A digital reconstruction of the original signal is then produced by the microcomputer, which through the use of digital feedback information removes the gain and adds the offset voltages back to the signal.

Feedback from microcomputer 16 to I/O circuit 14 is also required to maintain the values for the offset subtraction voltage, gain, and driver currents at levels appropriate to produce optimal A/D converter 106 resolution. Proper control requires that the microprocessor continually analyze, and response to, the offset subtraction voltage, gain, driver currents, and the output of A/D converter in a manner to be described next.

Briefly, with reference to FIG. 15, thresholds L1 and L2 slightly below and above the maximum positive and negative excursions L3 and L4 allowable for the A/D converter 106 input, are established and monitored by microcomputer 16 at the A/D converter 106 output. When the magnitude of the signal input to, and output from, A/D converter 106 exceeds either of the thresholds L1 or L2, the driver currents $I_D$ are readjusted to increase or decrease the intensity of light impinging upon the detector 38. In this manner, the A/D converter 106 is not overdriven and the margin between L1 and L3 and between L2 and L4 helps assure this even for rapidly varying signals. An operable voltage margin for A/D converter 106 exists outside of the thresholds, allowing A/D converter 106 to continues operating while the appropriate feedback adjustments to A and $V_{OS}$ are made.

When the signal from A/D converter 106 exceeds positive and negative thresholds L5 or L6, microcomputer 16 responds by signaling the programmable subtractor 100 to increase or decrease the offset voltage being subtracted. This is done through the formation and transmission of an offset code whose magnitude is dependent upon the level of the signal received from converter 106.

The manner in which the various thresholds are established and the relationship of the offset codes to the signal received can be altered to produce substantially any form of control desired. Thus, the arrangement shown in FIG. 15 is illustrative only and represents the currently preferred embodiment.

Figure 16:
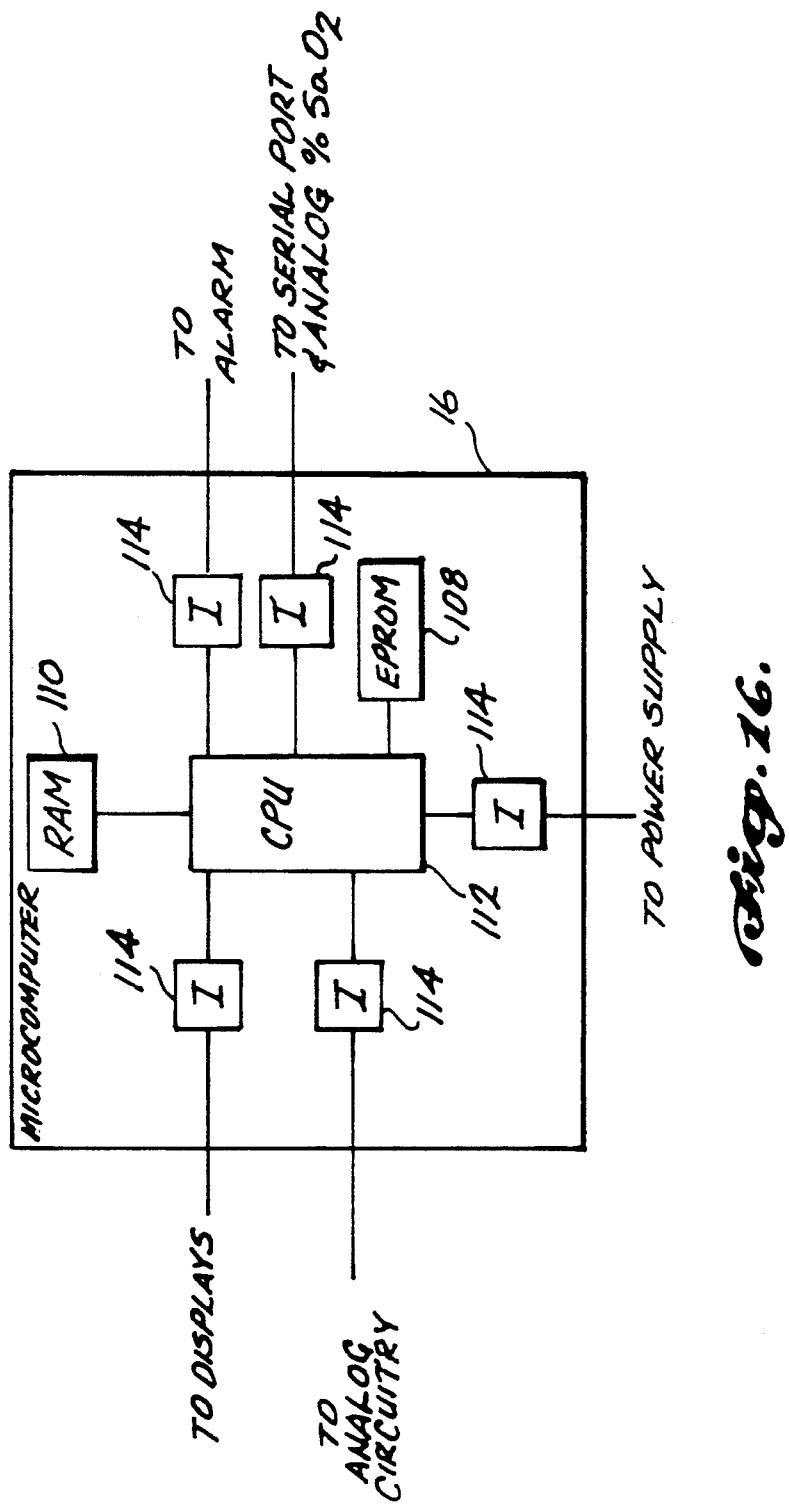
FIG. 16 is a more complete schematic diagram of the microcomputer illustrated in FIG. 1.

As will be appreciated from FIG. 16, the instructions for the microcomputer program that controls the signal construction-reconstruction discussed above are stored in erasable, programmable, read-only memory (EPROM) 108 of microcomputer 16. Similarly, values for $R_H$, $IR_HR_L$ and $IR_L$ are determined pursuant to peak-detection software contained in EPROM 108. These values are stored in random-access memory (RAM) 110 for operation upon by a central processing unit (CPU) 112 in accordance with further computational instructions stored in EPROM 108. Interfaces 114 act as input and output buffers for microcomputer 16.

The computational software in EPROM 108 initially causes CPU 112 to determine the present value for $R_{OS}$ by substituting the measured values for $R_H$, $IR_H$, $R_L$, and $IR_L$ into equation (22):

$$R_{OS} = \frac{\ln(R_L/R_H)}{\ln(IR_L/IR_H)} \quad (23)$$

Then, the computational software instructs CPU 112 to determine the oxygen saturation from $R_{OS}$ by use of a calibration curve selected from a family of curves in the following manner.

The calibration curve is a plot of the relationship between independently determined actual oxygen saturations, produced by the analysis of drawn blood samples, and the corresponding values of $R_{OS}$, produced by oximeter 10 in accordance with the technique described above. As shown in FIG. 17, a family of such curves includes a zero-compensation reference curve designated by a code $C_0$. The calibration curve identified by code $C_0$ is the plot of $R_{OS}$ versus oxygen saturation for the combination of LEDs 40 and 42 having predetermined reference wavelength light emissions, when those LEDs are operated at a predetermined reference temperature. If the response received by microcomputer 16 from coding resistor 52 and temperature sensor 50 indicates that sensor 12 does not have the predetermined reference wavelength LEDs or is not at the reference temperature, the calibration curve identified by code $C_0$ may no longer produce an accurate indication of the oxygen saturation from the value of $R_{OS}$ coupled. Thus, the difference in source light wavelength from the standards must be compensated for and is achieved in the following manner.

A code variable $C_N$ is established to identify the various curves in the family shown in FIG. 17. These curves are incrementally offset in each direction from the curve identified by code $C_0$. A sufficient number and arrangement of curves is included to accurately model the response produced by using any set of sorted LEDs 40 and 42 at any temperature within an expected operating range of 0° C. to 45° C. The appropriate curve is selected by determining the applicable code number $C_N$ in the following manner.

As noted previously, microcomputer 16 responds to information received from temperature sensor 50 and coding resistor 52. More particularly, the voltage drop across resistor 52, when supplied with a current of known magnitude or as part of a precision voltage divider, can be used to identify the resistance of resistor 52 and, hence, the combination of LEDs 40 and 42 included on sensor 12. This voltage represents $C_{CM}$, the compensation code for sensor M, and can be considered to include a component identifying the wavelength of light emitted by each LED, $C_{\lambda 1M}$ and $C_{\lambda 2M}$ at a reference temperature $T_0$.

Temperature sensor 50 produces an output having a magnitude that is proportional to the temperature sensed, T, in degrees Kelvin (°K.). A compensation code $C_{CT}$ can be determined from this information by multiplying a temperature compensation coefficient C by the difference between T and the probe reference temperature $T_0$ in °K.

Together, the probe compensation code $C_{CM}$ and temperature compensation code $C_{CT}$, indicate the adjustment to the zero-compensation reference curve $C_0$ needed to allow the oxygen saturation to be accurately determined from a given value for $R_{OS}$. Thus, a simple compensation code total, $C_T$, can be defined as:

$$C_T = C_{CM} + C_{CT} + C_0 \quad (24)$$

Allowing for nonlinearities as well as variable dependencies, equation (24) can be more completely expressed as:

$$C_T = F_a(C_{\lambda 2M})\Sigma a_i C_{\lambda M}^i + F_b(C_{\lambda 1M})\Sigma b_i C_{\lambda 2M}^i + \quad (25)$$
$$F_c(C_{\lambda 1M}, C_{\lambda 2M})\Sigma c_i(T - T_0)^i$$

where $a_i$, $b_i$, and $c_i$ are scaling constants; $F_a$, $F_b$, and $F_c$ are dependency correlating functions derived from modeled theory as well as empirical tests; and the summations are performed over a range of i extending from zero to n, with the summed terms being the power series approximation of the desired function. Note that equation (25) can be placed in linear form, corresponding to equation (24), as:

$$C_T = a_1 C_{\lambda 1M} + b_1 C_{\lambda 2M} + C_1(T - T_0) + C_0 \quad (26)$$

With the compensation code that $C_T$ determined, a compensated indication of oxygen saturation can be produced in accordance with the expression:

$$SaO_{2C} = \sum_{j=0}^{n} \left[ R_{OS}^j \sum_{i=0}^{m} [a_{i+j(m+1)}] C_T^i \right] \quad (27)$$

where $SaO_{2c}$ is the compensated nominal value of $SaO_2$; $a_{i+j(m+1)}$ is the scaling coefficient at $i+n(m+1)$; the sum of $R_{OS}^j$ from $j=0$ to $j=n$ is the power series approximation to $SaO_2$ to degree n; the sum of $a_{i+j(m+1)} C_T^i$ from $i=0$ to $i=m$ is the power series approximation of the compensating coefficient for $R_{OS}^j$ of degree m; i and j are integer values; and m and n are degrees of approximation.

By appropriate establishment of the zero-compensation code and temperature compensation coefficient, as well as the proper conditioning of information received from temperature sensor 50 and coding resistor 52, the resultant value of $C_T$ from equation (25) will indicate which of the curves in family $C_F$ allows the oxygen saturation to be most accurately determined. When a limited number of curves have been independently determined, and interpolation between curves is not employed, the curve to be used, $C_N$, is determined from $C_T$ by rounding $C_T$ to the nearest integer.

As will be appreciated, the values for $C_0$, $T_0$, C, and the various values for $C_{CM}$, depend upon a variety of factors, including the temperature-dependency of the wavelengths of light produced by LEDs 40 and 42. Thus, the manner of identifying the various curves of family $C_F$ shown in FIG. 17, as well as the number and orientation of the curves, may be varied and a suitable arrangement may best be determined by empirical studies.

The software that processes information received from temperature sensor 50 and coding resistor 52 and determines the applicable calibration curve $C_N$ is contained in EPROM 108. The software basically performs the computation set out in equation (25) and then rounds the resultant number to the nearest integer to determine $C_N$. The details of software capable of achieving such a result will be readily apparent to one of ordinary skill and, as such, are not presented here.

To generate a compensated curve, the coefficients and appropriate formulae for describing the nominal relationship between $R_{OS}$ and $SaO_2$ are stored in EPROM 108. After CPU 112 process information from the wavelength coding resistor 52 and temperature sensor 50 in sensor 12, the software solves a series of equations determining both the minimum and maximum values of $R_{OS}$ that can be produced for the spectrum of sensor codes and temperature range possible. As shown in FIG. 17, these minimum and maximum values of $R_{OS}$ producible by oximeter 10 correspond to oxygen saturation of 100 and 0 percent, respectively.

Next, the software instructs CPU 112 to compute the compensation formula given in equation (27). With this compensation value the nominal curve, or relationship between $R_{OS}$ and $SaO_2$, is modified to generate a compensated conversion formula. This compensated relationship is then used to generate a look-up table of sufficient resolution to guarantee a mapping of $R_{OS}$ with respect to $SaO_2$ such that the table includes every $SaO_2$ in one-percent increments from 0–100% $SaO_2$. When an actual $SaO_2$ prediction is to be made, a look-up algorithm transforms the ratio computed for equation (23) into a table index allowing the appropriate $SaO_2$ to be extracted from the table. This technique is employed to afford a run-time computational economy. The table need not be regenerated unless a different sensor with a new sensor code is used with the oximeter or when the temperature sensor 50 indicates a change in the ambient temperature that requires a curve shift to preserve predictive accuracy.

The peak-detection software in EPROM 108 also causes CPU 112 to determine the period of the signals received by microcomputer 16 from I/O circuit 14. Pursuant to the computational instructions in EPROM 108, CPU 112 then determines the pulse rate of the arterial blood flowing in the finger to be the inverse of the signal period. Displays 20 provide visible and audible outputs of the oxygen saturation and pulse rate in a manner conveniently used by the operator of oximeter 10.

While the references have been described with reference to a preferred embodiment, it is to be clearly understood by those skilled in the art that the invention is not limited thereto, and that the scope of the invention is to be interpreted only in conjunction with the following claims.

The embodiments of the invention in which an exclusive property or privilege is claimed are defined as follows:

1. An oximeter sensor comprising:

first and second light sources for illuminating tissue having arterial blood flowing therein, the light produced by each of said first and second sources being at a separate temperature dependent wavelength;

temperature indication means for producing an output indicative of the temperature of said first and second light sources;

light detection means, responsive to the illumination of said tissue, for producing signals that are proportional to the intensity of the light received at each of said temperature dependent wavelengths;

red optical filter means for filtering said light received by said light detection means;

and a sensor housing to which said first and second light sources, said temperature detection means, and said light detection means are connected.

2. An oximeter sensor comprising:

first and second light sources for illuminating tissue having arterial blood flowing therein, the light produced by each of said first and second sources being at a separate temperature dependent wavelength;

temperature indication means for producing an output indicative of the temperature of said first and second light sources;

light detection means, responsive to the illumination of said tissue, for producing signals that are proportional to the intensity of the light received at each of said temperature dependent wavelengths;

a reflective member positioned between said light detection means and said first and second light sources;

a sensor housing to which said first and second light sources, said temperature detection means, and said light detection means are connected, wherein said sensor housing comprises first and second elements, said first and second elements being attached to said first element and said light detection means attached to said second element, said first and second elements arranged to allow insertion of said tissue therebetween and to define a light path between said first and second light sources and said light detection means that includes said tissue, said light path including a first segment defined between said first and second light sources and said reflective member and a second segment defined between said reflective member and said light detection means, said first and second segments of said light path being at a predetermined angle to each other.

3. The sensor assembly of claim 2, wherein said first and second elements of said sensor housing are pivotally connected in a closably biased manner.

* * * * *

UNITED STATES PATENT AND TRADEMARK OFFICE
CERTIFICATE OF CORRECTION

Page 1 of 3

PATENT NO. : 5,259,381
DATED : November 9, 1993
INVENTOR(S) : P. W. Cheung et al.

It is certified that error appears in the above-indentified patent and that said Letters Patent is hereby corrected as shown below:

| COLUMN | LINE | |
|---|---|---|
| [57] "Abstract" | 4 | "source" should read --sources-- |
| 1 | 26 | "case" should read --care-- |
| 3 | 2 | "Wilker" should read --Wilber-- |
| 4 | 1 | "techniques" should read --technique-- |
| 7 | 7 | "ha" should read --has-- |
| 7 | 11 | "While" should read --With-- |
| 7 | 47 & 48 | "exces-sively" should read --exclusively-- |
| 8 | 23 | after "in" delete "the" |
| 8 | 54 | after "of" insert --the-- |
| 9 | 17 | "approximately" should read --approximating-- |
| 10 (Equation 15) | 37 & 38 | "$\dfrac{R_L}{R_H} = \dfrac{I_0 e^{-[\alpha d + \alpha A \Delta d]}}{I_0 e^{-\Delta d}} @^\lambda R = e^{-\alpha A \Delta d} @^\lambda R$" should read --$\dfrac{R_L}{R_H} = I_0 e \dfrac{-[\alpha d + \alpha_A \Delta d]}{I_0 e^{-\Delta d}} @^\lambda R = e^{-\alpha}A^{\Delta d} @^\lambda R$-- |
| 10 (Equation 16) | 44 | "$\ln(R_L/R_H) = \ln(e^{-\alpha A \Delta d})@^\lambda R = -\alpha_A \Delta d @ \lambda_R$" should read --"$\ln(R_L/R_H) = \ln(e^{-\alpha}A^{\Delta d})@^\lambda R = -\alpha_A \Delta d @ \lambda_R$"-- |

UNITED STATES PATENT AND TRADEMARK OFFICE
CERTIFICATE OF CORRECTION

PATENT NO. : 5,259,381
DATED : November 9, 1993
INVENTOR(S) : P. W. Cheung et al.

It is certified that error appears in the above-indentified patent and that said Letters Patent is hereby corrected as shown below:

| COLUMN | LINE | | |
|---|---|---|---|
| 10 (Equation 17) | 52 | "$IR_L = I_0 e^{-[\alpha d + \alpha A \Delta d]}@\lambda_{IR}$" should read --"$IR_L = I_0 e^{-[\alpha d + \alpha_A \Delta d]}@\lambda_{IR}$"-- | |
| 10 (Equation 18) | 57 | "$IR_H = I_0 e^{-\alpha d}@IR$" should read --$IR_H = I_0 e^{-\alpha d}@\lambda_{IR}$-- | |
| 10 (Equation 19) | 63 & 64 | "$\dfrac{IR_L}{IR_H} = \dfrac{I_0 e^{-[\alpha d + \alpha A \Delta d]}}{I_0 e^{-\alpha d}}@\lambda IR = e^{-\alpha A \Delta d}@\lambda IR$" should read --$\dfrac{IR_L}{IR_H} = \dfrac{I_0 e^{-[\alpha d + \alpha_A \Delta d]}}{I_0 e^{-\alpha d}}@\lambda IR = e^{-\alpha_A \Delta d}@\lambda IR$-- | |
| 10 (Equation 20) | 68 | "$\ln(IR_L/IR_H) = \ln(e^{-\alpha A \Delta d})@\lambda_{IR} = -\alpha_A \Delta d @\lambda_{IR}$" should read --$\ln(IR_L/IR_H) = \ln(e^{-\alpha_A \Delta d})@\lambda_{IR} = -\alpha_A \Delta d @\lambda_{IR}$-- | |
| 11 | 8 | "$\Delta$term" should read --$\Delta d$ term-- | |
| 11 | 29 | "Wilker" should read --Wilber-- | |
| 11 | 44 | "can s" should read --can-- | |
| 12 | 26 | "affects" should read --artifact-- | |
| 12 | 45 | "retain" should read --retainer-- | |

UNITED STATES PATENT AND TRADEMARK OFFICE
CERTIFICATE OF CORRECTION

PATENT NO. : 5,259,381
DATED : November 9, 1993
INVENTOR(S) : P. W. Cheung et al.

It is certified that error appears in the above-indentified patent and that said Letters Patent is hereby corrected as shown below:

| COLUMN | LINE | |
|---|---|---|
| 12 | 46 | "improve" should read --impinge-- |
| 12 | 64 | "pack" should read --peak-- |
| 14 | 22 | "different" should read --differential-- |
| 15 | 14 | "multiplex 104" should read --multiplexer 104-- |
| 15 | 51 | "case" should read --care-- |
| 16 | 22 & 23 | "microprocessor" should read --microcomputer-- |
| 16 | 23 | "response" should read --respond-- |
| 16 | 41 | "continues" should read --continue-- |
| 16 | 64 | "$IR_H R_L$" should read --$IR_H, R_L$-- |
| 18 | 35 | "$R_{OS}1$" should read --$R_{OS}^j$-- |
| 18 | 36 | "to" should read --of-- |
| 18 | 37 | "$C_T^1$" should read --$C_T^i$-- |
| 18 | 38 | "$R_{OS}j$" should read --$R_{OS}^j$-- |

Signed and Sealed this

Fifteenth Day of November, 1994

Attest:

BRUCE LEHMAN

Attesting Officer    Commissioner of Patents and Trademarks